(12) United States Patent
Purdy et al.

(10) Patent No.: US 11,052,237 B2
(45) Date of Patent: Jul. 6, 2021

(54) SWIVEL HUB

(71) Applicant: DFine, Inc., South Jordan, UT (US)

(72) Inventors: Craig Purdy, Sunnyvale, CA (US);
Dan Balbierz, Redwood City, CA (US);
Nate Shirley, Pleasant Grove, UT (US);
Gregory R. McArthur, Sandy, UT (US)

(73) Assignee: DFine, Inc., South Jordan, UT (US)

( * ) Notice: Subject to any disclaimer, the term of this patent is extended or adjusted under 35 U.S.C. 154(b) by 0 days.

(21) Appl. No.: 15/812,580

(22) Filed: Nov. 14, 2017

(65) Prior Publication Data
US 2018/0140821 A1    May 24, 2018

Related U.S. Application Data

(60) Provisional application No. 62/425,459, filed on Nov. 22, 2016.

(51) Int. Cl.
*A61M 39/10* (2006.01)
*F16L 27/093* (2006.01)

(52) U.S. Cl.
CPC .......... *A61M 39/105* (2013.01); *A61M 39/10* (2013.01); *A61M 39/1055* (2013.01); *F16L 27/093* (2013.01); *F16L 2201/40* (2013.01)

(58) Field of Classification Search
CPC ............ A61M 39/105; A61M 39/1055; A61M 39/10; A61M 39/26; F16L 27/093; F16L 2201/40
See application file for complete search history.

(56) References Cited

U.S. PATENT DOCUMENTS

| 3,125,360 A | * | 3/1964 | Ulrich | F16L 27/093 |
| | | | | 285/124.5 |
| 3,140,623 A | | 7/1964 | Hoose | |
| 3,147,015 A | * | 9/1964 | Hanback | F16L 17/08 |
| | | | | 277/622 |
| 3,244,439 A | * | 4/1966 | Montesi | F16L 33/223 |
| | | | | 285/148.15 |
| 3,384,394 A | * | 5/1968 | O'Connor | F16L 5/10 |
| | | | | 285/190 |
| 4,411,266 A | | 10/1983 | Cosman | |

(Continued)

FOREIGN PATENT DOCUMENTS

| CN | 2841051 | 11/2006 |
| JP | 2004242936 | 9/2004 |

(Continued)

OTHER PUBLICATIONS

International Search Report and Written Opinion dated Feb. 27, 2018 for PCT/US2017/061560.

(Continued)

*Primary Examiner* — Craig J Price
*Assistant Examiner* — Andrew J Rost
(74) *Attorney, Agent, or Firm* — Stoel Rives LLP

(57) ABSTRACT

The present disclosure relates to a connector for medical devices. The connector may have two interfaces facing different planes. The two interfaces may provide access to the connector's core and hub. The hub may be free to rotate relative to the core to increase accessibility and/or angle attachment while maintaining a fluid pathway between the core and the hub.

19 Claims, 8 Drawing Sheets

(56) References Cited

U.S. PATENT DOCUMENTS

| | | | |
|---|---|---|---|
| 4,456,017 A | 6/1984 | Miles | |
| 4,476,861 A | 10/1984 | Dimakos et al. | |
| 4,595,006 A | 6/1986 | Burke et al. | |
| 4,672,998 A | 6/1987 | Kozak, III | |
| 5,103,804 A | 4/1992 | Abele | |
| 5,282,821 A | 2/1994 | Donahue | |
| 5,284,128 A | 2/1994 | Hart | |
| 5,322,505 A | 6/1994 | Krause et al. | |
| 5,389,073 A | 2/1995 | Imran | |
| 5,437,636 A | 8/1995 | Snoke et al. | |
| 5,449,351 A | 9/1995 | Zohmann | |
| 5,458,597 A | 10/1995 | Edwards et al. | |
| 5,571,088 A | 11/1996 | Lennox | |
| 5,599,346 A | 2/1997 | Edwards et al. | |
| 5,620,447 A | 4/1997 | Smith et al. | |
| 5,620,467 A | 4/1997 | Wagner | |
| 5,628,771 A | 5/1997 | Mizukawa et al. | |
| 5,637,090 A | 6/1997 | McGee | |
| 5,662,680 A | 9/1997 | Desai | |
| 5,695,513 A | 12/1997 | Johnson et al. | |
| 5,697,536 A | 12/1997 | Eggers et al. | |
| 5,810,804 A | 9/1998 | Gough | |
| 5,833,632 A | 11/1998 | Jacobsen et al. | |
| 5,851,212 A | 12/1998 | Zirps et al. | |
| 5,855,577 A | 1/1999 | Murphy-Chutorian et al. | |
| 5,891,027 A | 4/1999 | Tu | |
| 5,902,251 A | 5/1999 | Vanhooydonk | |
| 5,921,956 A | 7/1999 | Grinberg et al. | |
| 5,928,239 A | 7/1999 | Mirza | |
| 5,944,715 A | 8/1999 | Goble et al. | |
| 5,947,964 A | 9/1999 | Eggers | |
| 6,064,902 A | 5/2000 | Haissaguerre | |
| 6,073,051 A | 6/2000 | Sharkey et al. | |
| 6,106,524 A | 8/2000 | Eggers et al. | |
| 6,123,702 A | 9/2000 | Swanson | |
| 6,135,999 A | 10/2000 | Fanton et al. | |
| 6,231,615 B1 | 5/2001 | Preissman | |
| 6,280,441 B1 | 8/2001 | Ryan | |
| 6,409,722 B1 | 6/2002 | Hoey et al. | |
| 6,440,138 B1 | 8/2002 | Reiley et al. | |
| 6,447,506 B1 | 9/2002 | Swanson et al. | |
| 6,464,683 B1 | 10/2002 | Samuelson et al. | |
| 6,478,793 B1 | 11/2002 | Cosman et al. | |
| 6,575,969 B1 | 6/2003 | Rittman et al. | |
| 6,592,559 B1 | 7/2003 | Pakter et al. | |
| 6,602,248 B1 | 8/2003 | Sharps et al. | |
| 6,615,830 B1 | 9/2003 | Serowski et al. | |
| 6,622,731 B2 | 9/2003 | Daniel et al. | |
| 6,863,672 B2 | 3/2005 | Reiley et al. | |
| 6,881,214 B2 | 4/2005 | Cosman et al. | |
| 7,022,133 B2 | 4/2006 | Yee et al. | |
| 7,108,696 B2 | 9/2006 | Daniel et al. | |
| 7,156,843 B2 | 1/2007 | Skarda | |
| 7,156,845 B2 | 1/2007 | Mulier | |
| 7,186,234 B2 | 3/2007 | Dahla et al. | |
| 7,267,683 B2 | 9/2007 | Sharkey et al. | |
| 7,270,661 B2 | 9/2007 | Dahla et al. | |
| 7,480,533 B2 | 1/2009 | Cosman et al. | |
| 7,503,920 B2 | 3/2009 | Siegal | |
| 7,569,054 B2 | 8/2009 | Michelson | |
| 7,625,364 B2 | 12/2009 | Corcoran et al. | |
| 7,703,814 B2 * | 4/2010 | Wei | F16L 27/093 285/190 |
| 7,824,403 B2 | 11/2010 | Vaska | |
| 7,905,884 B2 | 3/2011 | Simonton et al. | |
| 8,246,627 B2 | 8/2012 | Vanleeuwen et al. | |
| 8,583,260 B2 | 11/2013 | Knudson | |
| 8,591,507 B2 | 11/2013 | Kramer et al. | |
| 8,663,226 B2 | 3/2014 | Germain | |
| 8,758,349 B2 | 6/2014 | Germain et al. | |
| 8,864,760 B2 | 10/2014 | Kramer et al. | |
| 9,113,974 B2 | 8/2015 | Germain | |
| 9,125,671 B2 | 9/2015 | Germain et al. | |
| 9,161,809 B2 | 10/2015 | Germain et al. | |
| 9,421,057 B2 | 8/2016 | Germain | |
| 2001/0003312 A1 * | 6/2001 | Spiegel | F16H 57/0413 165/283 |
| 2002/0026197 A1 | 2/2002 | Foley et al. | |
| 2002/0133148 A1 | 9/2002 | Daniel et al. | |
| 2003/0014094 A1 | 1/2003 | Hammack et al. | |
| 2003/0130664 A1 | 7/2003 | Boucher et al. | |
| 2003/0212394 A1 | 11/2003 | Pearson et al. | |
| 2003/0212395 A1 | 11/2003 | Woloszko et al. | |
| 2004/0087936 A1 | 5/2004 | Stern et al. | |
| 2004/0202505 A1 | 10/2004 | Pagliai | |
| 2004/0212193 A1 * | 10/2004 | Johnstone | F16L 27/093 285/390 |
| 2005/0055030 A1 | 3/2005 | Falahee | |
| 2005/0090852 A1 | 4/2005 | Layne et al. | |
| 2005/0177210 A1 | 8/2005 | Lueng et al. | |
| 2005/0216018 A1 | 9/2005 | Sennett | |
| 2006/0025763 A1 | 2/2006 | Nelson et al. | |
| 2006/0085009 A1 | 4/2006 | Truckai et al. | |
| 2006/0200121 A1 | 9/2006 | Mowery | |
| 2006/0264819 A1 | 11/2006 | Fischer et al. | |
| 2007/0006692 A1 | 1/2007 | Phan | |
| 2007/0055281 A1 | 3/2007 | Osorio et al. | |
| 2007/0156130 A1 | 7/2007 | Thistle | |
| 2007/0260257 A1 | 11/2007 | Phan | |
| 2007/0282305 A1 | 12/2007 | Goldfarb et al. | |
| 2008/0004615 A1 | 1/2008 | Woloszko et al. | |
| 2008/0012294 A1 | 1/2008 | Cheng | |
| 2008/0033422 A1 | 2/2008 | Turner et al. | |
| 2008/0058821 A1 | 3/2008 | Maurer et al. | |
| 2008/0183165 A1 | 7/2008 | Buysee et al. | |
| 2008/0183265 A1 | 7/2008 | Bly | |
| 2008/0208255 A1 | 8/2008 | Siegal | |
| 2008/0228192 A1 | 9/2008 | Beyer et al. | |
| 2008/0249525 A1 | 10/2008 | Lee et al. | |
| 2009/0146416 A1 | 6/2009 | Wei | |
| 2009/0264862 A1 | 10/2009 | Neidert et al. | |
| 2009/0264892 A1 | 10/2009 | Beyar et al. | |
| 2009/0293687 A1 | 12/2009 | Nino et al. | |
| 2009/0299282 A1 | 12/2009 | Lau et al. | |
| 2010/0082033 A1 | 4/2010 | Germain | |
| 2010/0121332 A1 | 5/2010 | Crainich et al. | |
| 2010/0152724 A1 | 6/2010 | Marion et al. | |
| 2010/0211076 A1 | 8/2010 | Germain et al. | |
| 2011/0034884 A9 | 2/2011 | Pellegrino et al. | |
| 2011/0098701 A1 | 4/2011 | McIntyre et al. | |
| 2011/0160737 A1 | 6/2011 | Steffen et al. | |
| 2011/0251615 A1 | 10/2011 | Truckai et al. | |
| 2011/0295261 A1 | 12/2011 | Germain | |
| 2011/0295262 A1 | 12/2011 | Germain et al. | |
| 2011/0297757 A1 | 12/2011 | Schmuckle | |
| 2011/0301590 A1 | 12/2011 | Podhajsky et al. | |
| 2012/0065543 A1 | 3/2012 | Ireland | |
| 2012/0130381 A1 | 5/2012 | Germain | |
| 2012/0191037 A1 * | 7/2012 | Patel | F16K 5/0407 604/30 |
| 2012/0239049 A1 | 9/2012 | Truckai | |
| 2012/0330180 A1 | 12/2012 | Pellegrino et al. | |
| 2012/0330301 A1 | 12/2012 | Pellegrino et al. | |
| 2013/0072941 A1 | 3/2013 | Tan-Malecki et al. | |
| 2013/0174918 A1 * | 7/2013 | Rodrigues-Morgado | B60T 17/222 137/15.01 |
| 2013/0231654 A1 | 9/2013 | Germain | |
| 2013/0261615 A1 | 10/2013 | Kramer et al. | |
| 2013/0261621 A1 | 10/2013 | Kramer et al. | |
| 2013/0331692 A1 * | 12/2013 | Mouri | A61M 39/10 600/435 |
| 2014/0135779 A1 | 5/2014 | Germain | |
| 2014/0163566 A1 | 6/2014 | Phan et al. | |
| 2014/0350542 A1 | 11/2014 | Kramer et al. | |
| 2014/0371740 A1 | 12/2014 | Germain et al. | |
| 2015/0216594 A1 | 8/2015 | Prakash | |
| 2015/0297246 A1 | 10/2015 | Patel et al. | |
| 2015/0313614 A1 | 11/2015 | Germain | |
| 2016/0008639 A1 | 1/2016 | MacLeod et al. | |
| 2016/0228131 A1 | 8/2016 | Brockman et al. | |

(56) References Cited

U.S. PATENT DOCUMENTS

FOREIGN PATENT DOCUMENTS

| WO | 1993004634 | 3/1993 |
| WO | 1997003611 | 2/1997 |
| WO | 2003101308 | 12/2003 |
| WO | 2007036815 | 4/2007 |
| WO | 2008076330 | 6/2008 |
| WO | 2008084479 | 7/2008 |
| WO | 2010039894 | 4/2010 |
| WO | 2010081187 | 7/2010 |
| WO | 2010135602 | 11/2010 |
| WO | 2010135606 | 11/2010 |
| WO | 2011137357 | 11/2011 |
| WO | 2011137377 | 11/2011 |
| WO | 2012071464 | 5/2012 |
| WO | 2013147990 | 10/2013 |
| WO | 2014093673 | 6/2014 |
| WO | 2016027190 | 2/2016 |

OTHER PUBLICATIONS

European Search Report dated Nov. 15, 2017 for EP09818476.5.
European Search Report dated Nov. 16, 2016 for EP14772615.2.
International Search Report and Written Opinion dated Feb. 7, 2018 for PCT/US2017/058303.
International Search Report and Written Opinion dated Feb. 21, 2018 for PCT/US2017/063281.
International Search Report and Written Opinion dated Mar. 30, 2018 for PCT/US2017/065328.
International Search Report and Written Opinion dated Apr. 23, 2016 for PCT/US2018/012372.
International Search Report and Written Opinion dated Nov. 20, 2009 for PCT/US2009/059113.
Notice Allowance dated Jan. 18, 2017 for U.S. Appl. No. 13/097,998.
Notice Allowance dated Apr. 9, 2014 for U.S. Appl. No. 12/578,455.
Notice Allowance dated Apr. 23, 2018 for U.S. Appl. No. 13/083,411.
Notice Allowance dated Oct. 28, 2016 for U.S. Appl. No. 13/853,397.
Notice Allowance dated Nov. 8, 2013 for U.S. Appl. No. 12/578,455.
Notice Allowance dated Nov. 18, 2016 for U.S. Appl. No. 13/097,998.
Notice Allowance dated Nov. 25, 2013 for U.S. Appl. No. 12/571,174.
Notice Allowance dated Nov. 25, 2016 for U.S. Appl. No. 13/853,397.
Notice Allowance dated Dec. 13, 2018 for U.S. Appl. No. 15/917,454.
Notice Allowance dated Dec. 28, 2017 for U.S. Appl. No. 15/211,359.
Notice of Allowance dated Aug. 31, 2016 for U.S. Appl. No. 14/887,007.
Office Action dated Feb. 3, 2016 for U.S. Appl. No. 13/853,397.
Office Action dated Feb. 10, 2015 for U.S. Appl. No. 13/083,411.
Office Action dated Mar. 1, 2017 for U.S. Appl. No. 15/211,359.
Office Action dated May 24, 2012 for U.S. Appl. No. 12/578,455.
Office Action dated Jun. 4, 2018 for U.S. Appl. No. 15/349,715.
Office Action dated Jun. 22, 2018 for U.S. Appl. No. 15/917,454.
Office Action dated Jun. 25, 2015 for U.S. Appl. No. 13/853,397.
Office Action dated Jul. 12, 2017 for U.S. Appl. No. 13/083,411.
Office Action dated Jul. 30, 2013 for U.S. Appl. No. 13/083,411.
Office Action dated Sep. 6, 2017 for U.S. Appl. No. 15/211,359.
Office Action dated Oct. 30, 2018 for U.S. Appl. No. 15/349,715.
Office Action dated Nov. 12, 2013 for U.S. Appl. No. 13/083,411.
Office Action dated Nov. 25, 2016 for U.S. Appl. No. 13/083,411.
Office Action dated Dec. 3, 2012 for U.S. Appl. No. 12/571,174.
Office Action dated Feb. 27, 2013 for U.S. Appl. No. 12/578,455.
Office Action dated Jul. 12, 2016 for U.S. Appl. No. 14/887,007.
Office Action dated Sep. 10, 2013 for U.S. Appl. No. 12/571,174.
European Search Report dated Apr. 3, 2020 for EP17873790.4.

\* cited by examiner

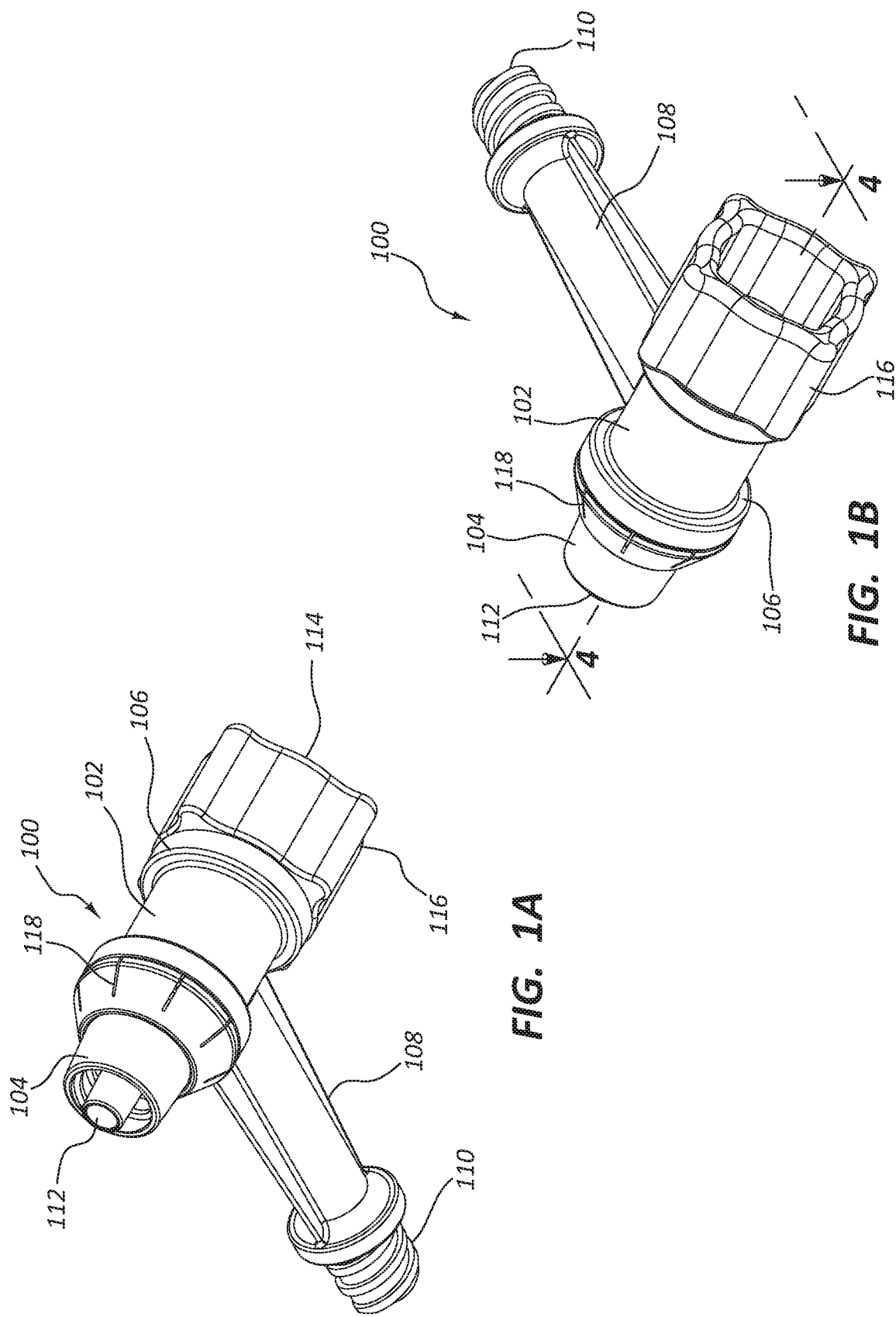

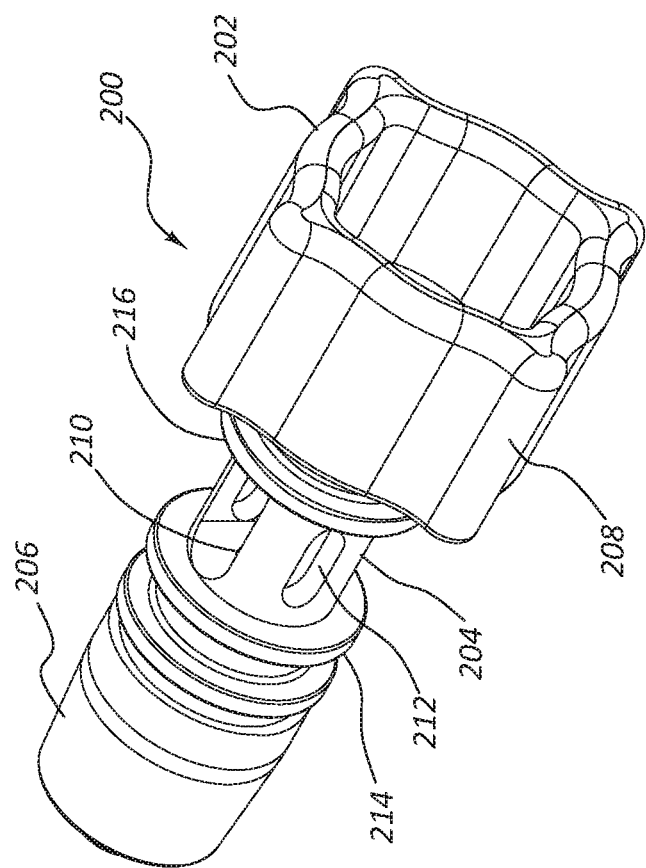
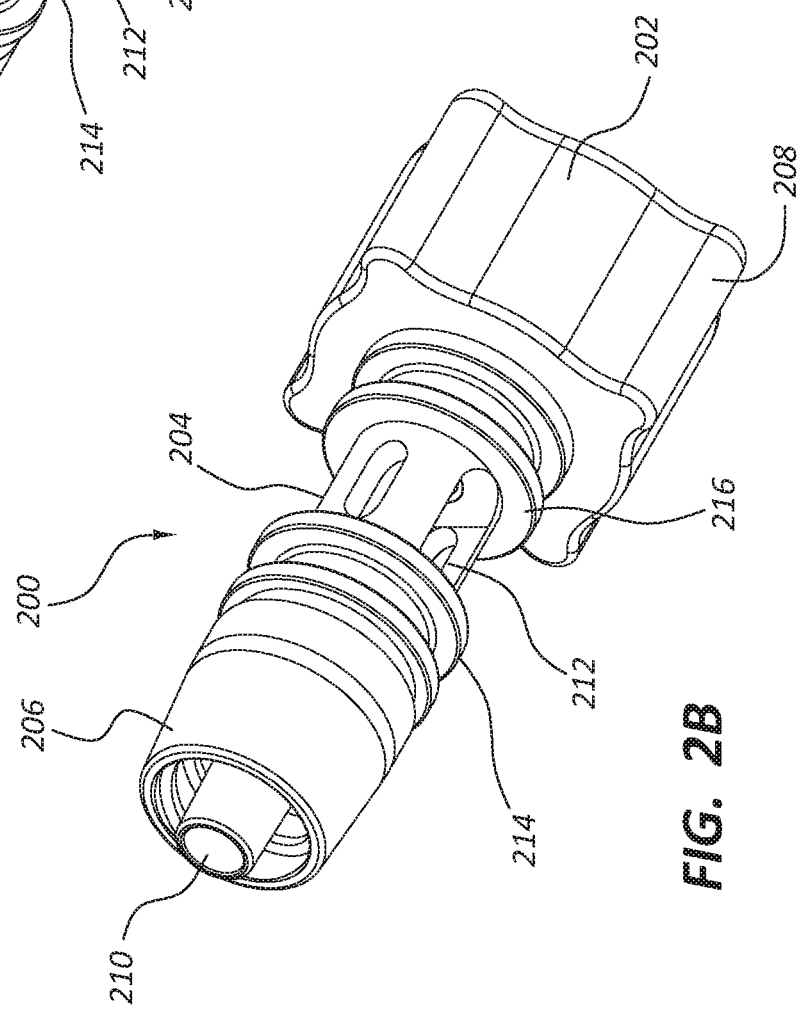
FIG. 2A
FIG. 2B

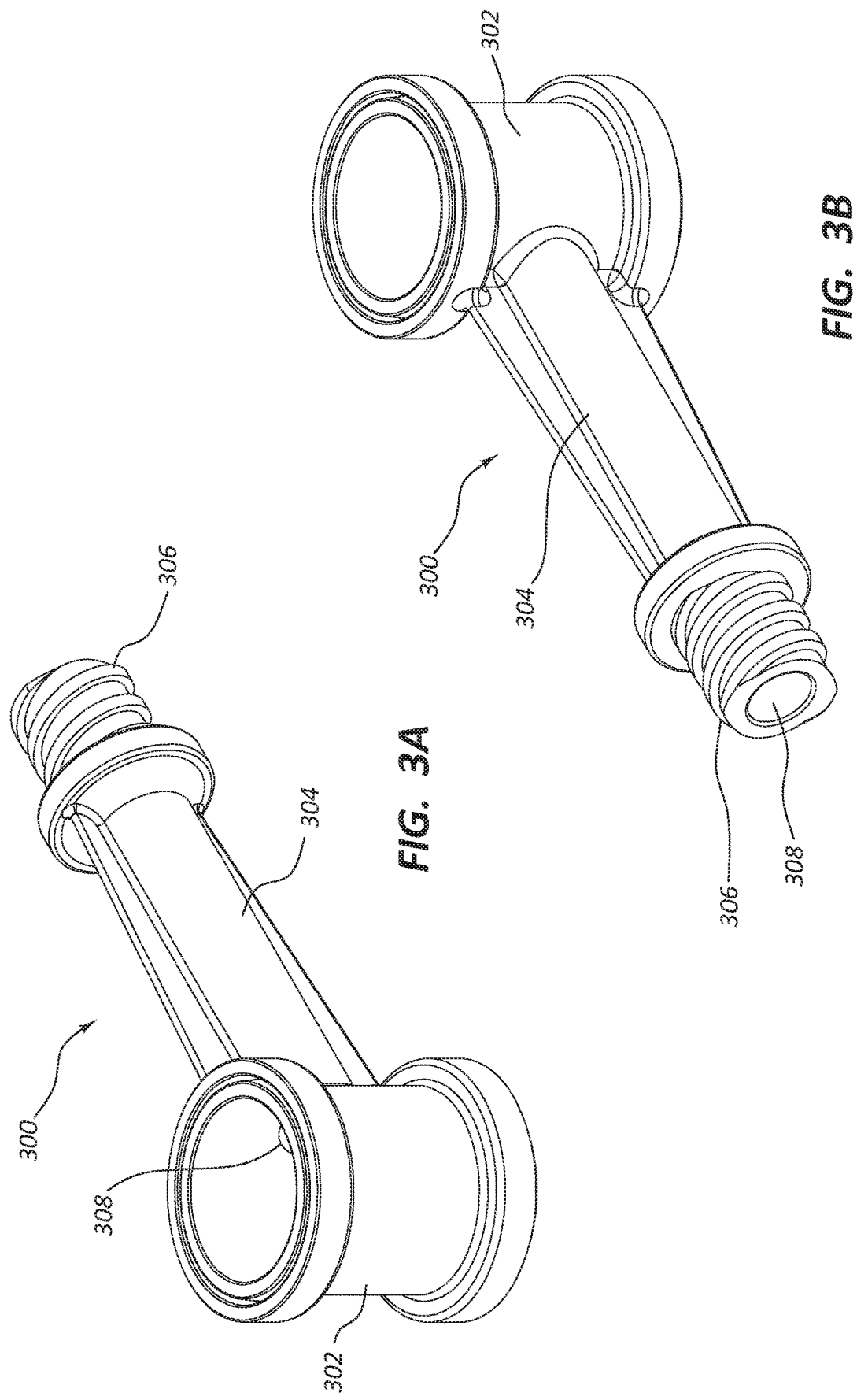

SWIVEL HUB

RELATED APPLICATIONS

This application claims priority to U.S. Provisional Application No. 62/425,459, filed on Nov. 22, 2016 and titled, "Swivel Hub," which is hereby incorporated by reference in its entirety.

TECHNICAL FIELD

The present disclosure relates generally to the field of medical devices. More particularly, embodiments disclosed herein relate to medical connectors and related systems and methods.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIGS. 1A and 1B are perspective views of a swivel elbow connector, according to one embodiment.

FIGS. 2A and 2B are perspective views of a core of a swivel elbow connector, according to one embodiment.

FIGS. 3A and 3B are perspective views of a hub of a swivel elbow connector, according to one embodiment.

DETAILED DESCRIPTION

Figure 4:
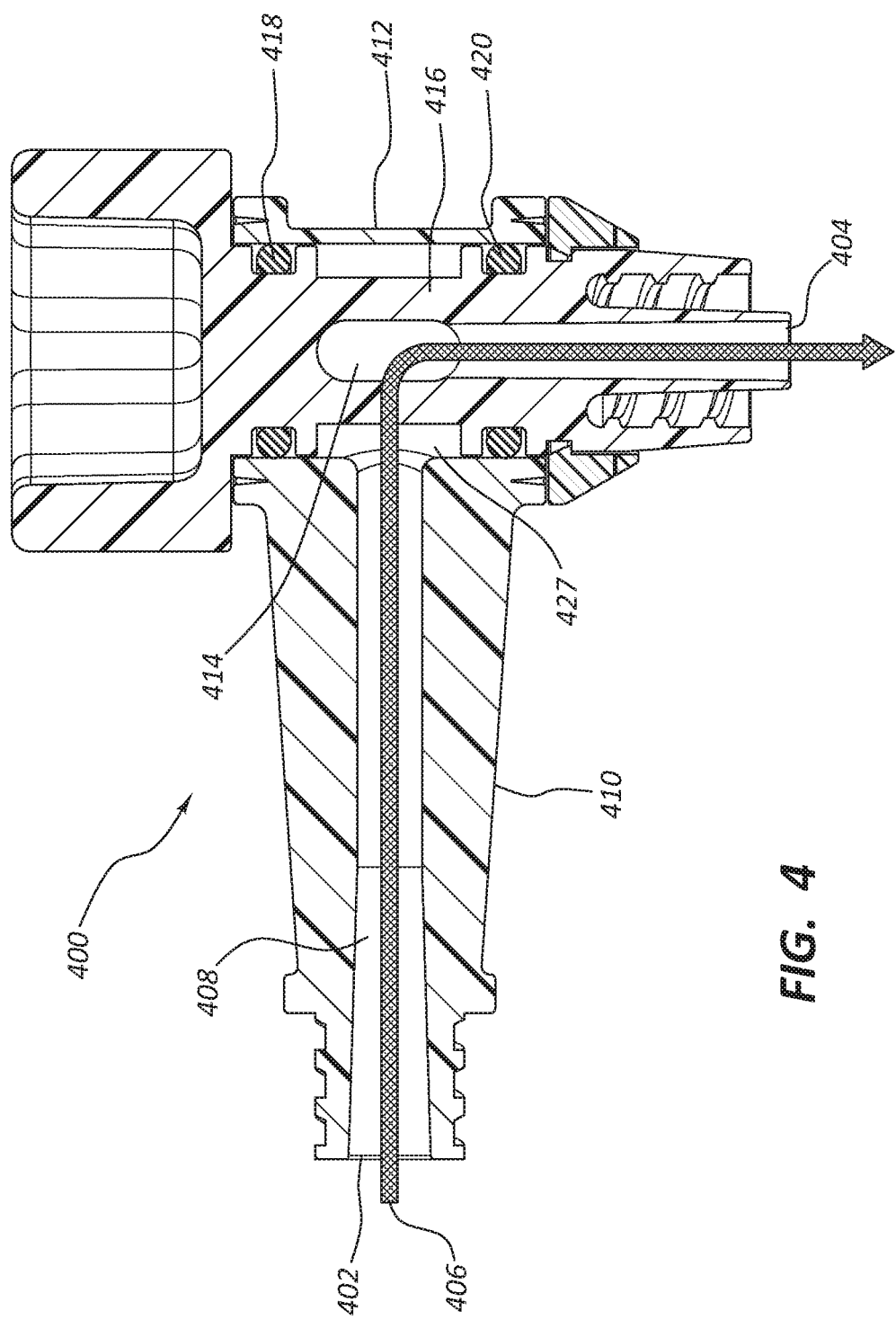
FIG. 4 is a cross sectional view of a swivel elbow connector, according to one embodiment.

This disclosure describes swivel hubs, such as a swivel elbow connector, and related systems and methods. A swivel elbow connector may include a core with a center cavity. At least one aperture may provide an opening to the center cavity in the core. A first interface may be mechanically coupled to the core and fluidly coupled with the center cavity in the core. A swivel elbow connector may include a hub that selectively rotates relative to the core and the first interface. The hub may include a sleeve that surrounds the core and a stem with a second interface that forms a port through the lateral surface of the hub. The swivel elbow connector may form a fluid pathway for transferring a fluid through the second interface, the hollow stem, the hub, the plurality of apertures in the core, and the first interface.

The angle and positioning of a medical device may limit the accessibility of its interfaces. Typical elbow connectors may be used to change the angle of an interface, however the rotation required to couple two luer connectors positioned at one or both ends of the elbow may cause the elbow to be positioned at an undesirable angle. Further, a typical elbow connector is rigid and stationary making any connected tubing susceptible to kinks and breaks if pulled.

A swivel elbow connector, as described herein, may increase the accessibility of a medical device interface without the detriments of a typical elbow connector. A rotatable hub may allow the angle of the swivel elbow connector to be adjusted to increase accessibility. Further, the rotatable hub may prevent kinks and breaks by rotating when a connected tube is pulled.

The rotatable hub may include a sleeve and a stem. The sleeve may be a barrel forming a chamber. For instance, in one embodiment, the sleeve may be plastic molded into a hollow cylinder with openings on both ends. The stem may be coupled to a lateral side of the sleeve and in fluid communication with the chamber. In one embodiment, the stem may be perpendicular to the sleeve. In alternate embodiments, the stem may protrude off the lateral side at angles other than 90 degrees. The chamber may be configured in size and shape to house the core.

The core may form a cavity and extend through the sleeve's chamber. The cavity may be in fluid communication with the chamber via one or more apertures in the core. In one embodiment, the core may have a plurality of apertures. The apertures may extend through the entire core.

The core may be sealed within the sleeve. For example, two O-rings may fluidly seal the sleeve to the core. A fastener and a gripping surface may retain the core within the sleeve. The fastener may be a snap-fit retaining ring, a threaded retaining ring, a lock nut, or a bonded joint. In one embodiment, the fastener may be adjusted to make the hub easier or more difficult to rotate.

The gripping surface may be rotatable and mechanically coupled to the core. A user may rotate the core using the gripping surface. The gripping surface may also rotate the first interface coupled to the core. The gripping surface may have an uneven surface to assist in rotating the core. For example, the gripping surface may have a plurality of grip tabs. Alternatively, the gripping surface may have a plurality of grooves.

Medical tools and devices may attach to the first and second interfaces of the swivel elbow connector. In one embodiment, the first interface may be a male luer and the second interface may be a female luer. In another embodiment, the first interface may be a different type than the second interface. A valve may limit dripping and leakage when either interface is disconnected.

Attached medical tools and devices may transfer material through the fluid pathway of the connector. In one embodiment, material may only flow when the stem is in line with an aperture in the core. Thus, the swivel elbow connector may selectively rotate between a lock position in which no material may pass and an unlocked position in which material may pass freely. In such an embodiment, the swivel elbow connector may provide tactile feedback when the position is changed. In another embodiment, the hub's sleeve and core are sized and positioned to allow material to surround the core and enter apertures not in line with the stem. Thus, the swivel elbow connector may allow for a continuous flow of material regardless of positioning.

The phrase "coupled to" is broad enough to refer to any suitable coupling or other form of interaction between two or more entities, including mechanical, fluidic and thermal interaction. Thus, two components may be coupled to each other even though they are not in direct contact with each other. The phrases "attached to" refers to interaction between two or more entities which are in direct contact with each other and/or are separated from each other only by a fastener of any suitable variety (e.g., mounting hardware or an adhesive).

The phrases "fluidly coupled" and "fluid communication" are broad enough to refer to arrangements in which a fluid (e.g., a gas or a liquid) can flow from one element to another element when the elements are in fluid communication with each other.

The terms "proximal" and "distal" are opposite directional terms. For example, the distal end of a device or component is the end of the component that is furthest from the physician during ordinary use. The proximal end refers to the opposite end, or the end nearest the physician during ordinary use.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

FIGS. 1A and 1B are perspective views of a swivel elbow connector 100, according to one embodiment. The swivel elbow connector 100 may include a hub 102 that freely rotates around a core 104. The ability of the hub 102 to rotate may allow a user to reposition the hub 102 for accessibility of coupling locations or interfaces 110, 112 described below.

The hub 102 may include a sleeve 106, a stem 108, and a first interface 110. As shown, the sleeve 106 may be a cylinder. The stem 108 may form a port through a lateral of the sleeve 106. The first interface 110 may be located at a proximal end of the stem 108. The sleeve 106 and the stem 108 may be hollow and form a first fluid pathway to allow material to pass from the first interface 110 to the sleeve 106.

As shown, the core 104 may extend through the sleeve 106. The core 104 may have a second fluid pathway in fluid communication with the first fluid pathway. The second fluid pathway in the core 104 may direct material from the first fluid pathway through a second interface 112.

The core 104 may also include a gripping surface 114. A user may rotate the gripping surface 114 to rotate the entire core 104. This may allow a user to rotate the core 104 without affecting the hub 102. For example, as shown the second interface 112 may be a threaded interface. To attach the second interface 112 to a medical tool, a user may rotate the gripping surface 114. Because the hub 102 may rotate freely, the rotation of the core 104 would not affect the hub's positioning. The gripping surface 114 may include a series of tabs 116 or grooves to improve handling. Additionally, once the core 104 is coupled to a medical tool, the hub 102 may still be free to rotate about the core 104 while still maintaining flow through from the first interface 110 to the second interface 112 (and flow from the second interface 112 to the first interface 110).

The first interface 110 may be at an angle relative to the second interface 112. As shown, the first interface 110 may be perpendicular to the second interface 112. In alternative embodiments, the angle between the first interface 110 and the second interface 112 may be different. In one embodiment, the stem 108 may be flexible to accommodate a variety of angles.

The first interface 110 and the second interface 112 may connect to a first and a second medical tool. For example, the first interface 110 may connect to a bone cement injector and the second interface 112 may connect to a cannula. The first interface 110 and the second interface 112 may be the same type. For example, as shown the first interface 110 and the second interface 112 may be a male and a female luer. In alternative embodiments swivel elbow connector 100 may be an adapter and the first interface 110 and the second interface 112 may be different types.

A fastener 118 may secure the hub 102 to the core 104. In some embodiments, the fastener 118 may be a snap-fit retaining ring or a threaded retaining ring. The fastener 118 may limit the movement of the hub 102 with respect to the core 104, allowing the hub 102 to rotate with respect to the core 104 but not translate with respect to the core 104.

FIGS. 2A and 2B are perspective views of a core 200 of a swivel elbow connector, according to one embodiment. The core 200 of FIGS. 2A and 2B is one example of a core 104 that may be used with the swivel elbow connector of FIGS. 1A and 1B. As shown, the core 200 may include a gripping surface 202, a junction 204, and an interface 206.

Various manufacturing techniques may be implemented to manufacture the core 200. In one embodiment, the core 200 may be one continuous piece. For example, the gripping surface 202, the junction 204, and the interface 206 may be molded as a single piece or etched from a single block. In another embodiment, the gripping surface 202, the junction 204, and the interface 206 may be separate pieces coupled together.

As shown, the gripping surface 202 may be attached to the junction 204, which may be attached to the interface 206. In alternative embodiments, the relative placement of the core 200 elements may be different. For example, a gripping surface may be built into the interface 206.

The gripping surface 202 may be a knob or handle to rotate the core 200. The core 200 may rotate to couple the interface 206 to a mating interface via threads. The gripping surface 202 may have an uneven surface for additional grip. For example, as shown, the gripping surface 202 may include a plurality of tabs 208. In alternative embodiments, the gripping surface 202 may include grooves or divots.

The core 200 may have a fluid passage way 210. The fluid passageway 210 may extend from the interface 206 to the junction 204. Material may enter or exit the fluid passageway 210 via an opening in the interface 206 and apertures 212 in the junction 204.

There may be a plurality of apertures 212 accessing the fluid passageway 210 from a variety of angles. In some embodiments, the apertures 212 may be elongated shapes for increased flow while maintaining structural integrity of the junction 204. In other embodiments, the apertures 212 may include a plurality of smaller holes arranged such that at least one aperture 212 will align with the stem of the hub at any given position.

When assembled, the junction 204 may be enclosed by the swivel elbow connector's hub. The junction 204 may include hub support members 214, 216 to couple to the hub. The support members 214, 216 may have a similar diameter as the hub's chamber to allow the hub to rotate with little play. In some embodiments, as shown, a portion of the junction 204 may have a smaller diameter than the support members 214, 216, forming an annular space between the smaller diameter portion of the junction 204 and a hub coupled to the core 200 (see annular space 427 of FIG. 4). In such an embodiment, material traveling through the connector may flow into the annular space and surround the smaller diameter portion and fill all of the apertures 212 and flow through the fluid passageway 210. The direction of flow could also be reversed, flowing from the passageway 210 to the annular space and out through a portion of a hub coupled to the core 200. In some alternative embodiments, an aperture would have to be in line with a hub's stem to allow material to flow through the fluid pathway.

FIGS. 3A and 3B are perspective views of a hub 300 of a swivel elbow connector, according to one embodiment. The hub 200 of FIGS. 3A and 3B is one example of a hub 102 that may be used with the swivel elbow connector of FIGS. 1A and 1B. The hub 300 may include a sleeve 302, a stem 304, and an interface 306.

Various manufacturing techniques may be implemented to manufacture the hub 300. In one embodiment, the core may be one continuous piece. For example, the sleeve 302, the stem 304, and the interface 306 may be molded as a single piece or etched from a single block. In another embodiment, the gripping surface 202, the sleeve 302, the stem 304, and the interface 306 may be separate pieces coupled together.

Separating the elements of the hub 300 may allow for the use of multiple materials. For example, in one embodiment the sleeve 302 may be made from a rigid plastic, to maintain a cylindrical shape, and the stem 304 may be made of a flexible or semi rigid material to increase accessibility to the interface 306.

The cylindrical shape of the sleeve 302 may allow the hub 300 to rotate around a core. In some embodiments the sleeve 302 may be able to rotate an entire 360 degrees. In another embodiment, the sleeve 302 may contain a limiter that limits the degree that the hub 300 can rotate around the core.

The hub 300 may have a fluid passageway 308. The fluid passageway 308 may extend from the interface 306 through the stem 304 to the sleeve 302. Material may enter or exit the fluid passageway 308 via an opening in the interface 306 and an opening in the sleeve 302.

FIG. 4 is a cross sectional view of a swivel elbow connector 400, according to one embodiment. This cross sectional view is one example of a cross sectional view of the swivel elbow connector 100 of FIGS. 1A and 1B. As shown in FIG. 4, a material 406 may travel from a first interface 402 to a second interface 404 through a fluid passageway 408.

As shown, the material 406 may enter the first interface 402. The material 406 may be introduced by a medical tool coupled to the first interface 402. After the material 406 enters the first interface 402, it may travel through the fluid passageway 408 down a stem 410 to reach a sleeve 412. An annular space 427 may be disposed between an inside diameter of the sleeve 412 and an outside diameter of a core 416 disposed within the sleeve 412. The material 406 may then enter apertures 414 of a core 416. The material 406 may then exit the second interface 404. O-rings 418, 420 may seal the sleeve 412 to prevent the material 406 from leaking from the annular space 427 out of the sleeve 412.

While FIG. 4 depicts the material 406 traveling in one direction, in some embodiments the swivel elbow connector 400 may allow the material 406 to move in either direction, that is from the first interface 402 to the second interface 404 or from the second interface 404 to the first interface 402. In alternative embodiments, a valve may limit the flow or direction of the material.

Figure 5:
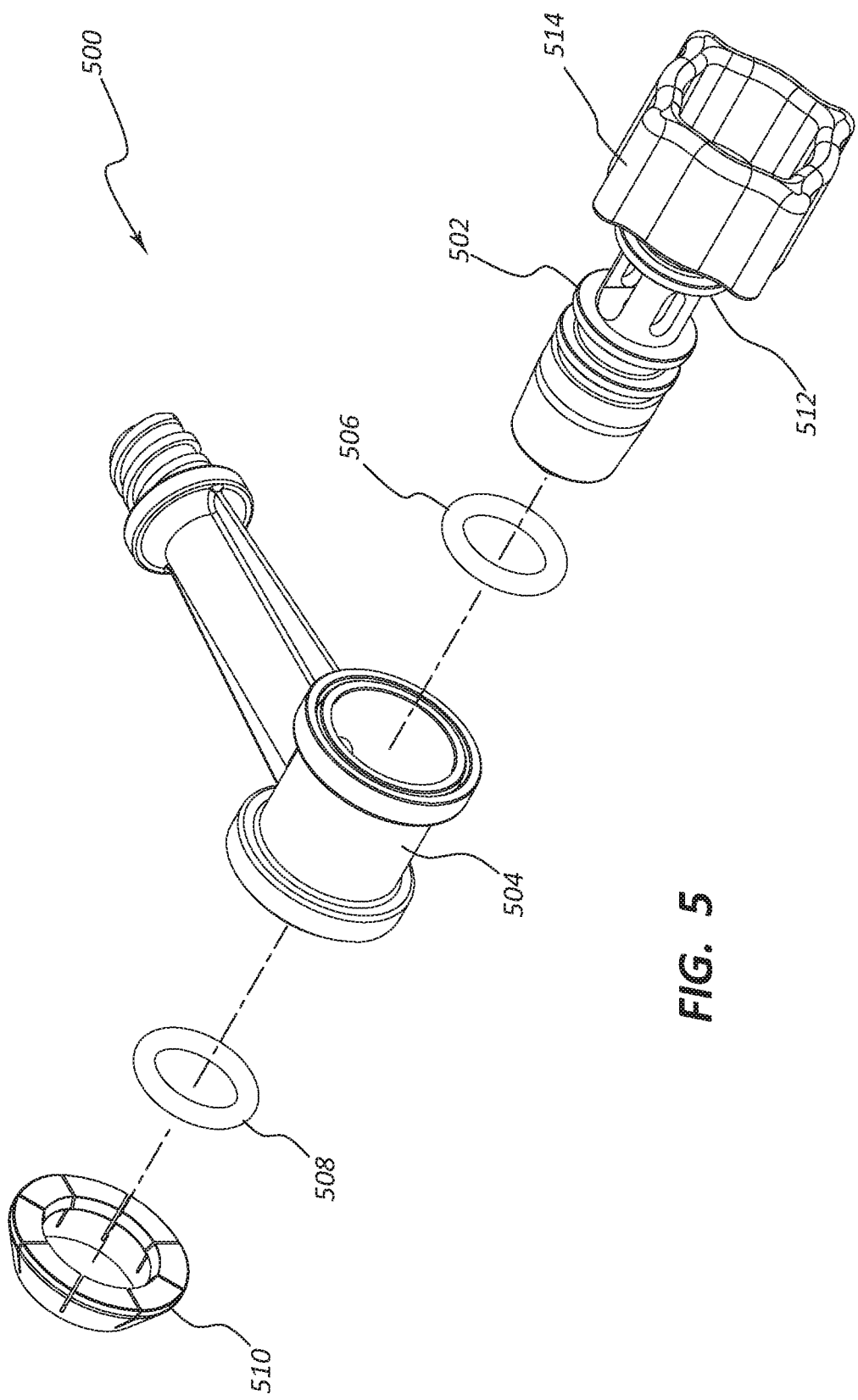
FIG. 5 is an exploded view of a swivel elbow connector, according to one embodiment.

FIG. 5 is an exploded view of a swivel elbow connector 500, according to one embodiment. This exploded view is one example of components that may be used with the swivel elbow connector 100 of FIGS. 1A and 1B or the swivel elbow connector 400 of FIG. 4. The swivel elbow connector 500 may be assembled with a core 502, a hub 504, two O-rings 506 and 508, and a snap ring 510. An assembler may place the O-ring 506 on the core 502. Grooves 512 and a gripping surface 514 may assist in the O-ring 506 placement. An assembler may then place the hub 504 on the core 502. The hub 504 may align with the core 502 such that they are in fluid communication. O-rings 506 and 508 may fluidly seal the hub 504 to the core 502. The snap ring 510 may retain the hub 504 in position.

Figure 6:
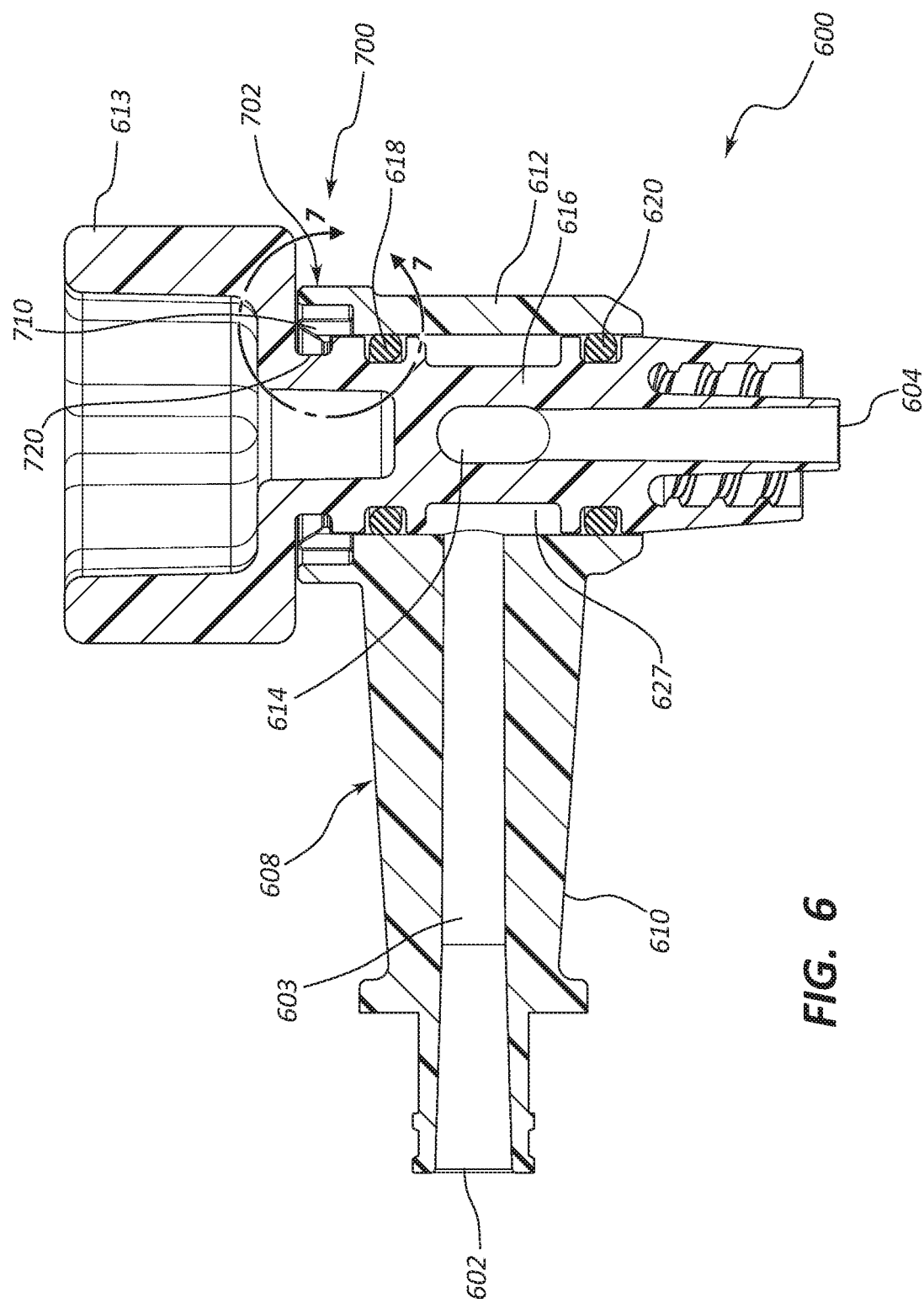
FIG. 6 is a cross sectional view of a swivel elbow connector with an integrated retaining ring, according to one embodiment.

FIG. 6 is a cross sectional view of a swivel elbow connector 600 with an integrated retaining ring 702, according to one embodiment. Various features recited in connection with embodiments illustrated in FIGS. 1-5 may be used in connection with the swivel elbow connector 600 and vice versa. Features of each embodiment may be understood as applying analogously to the other embodiments.

For example, similar to the embodiments discussed in the previous figures, the swivel elbow connector 600 may comprise a hub 608 and a core 616 with a gripping surface 613. Material may enter the first interface 602, and travel through a fluid passageway 603 down a stem 610 to reach a sleeve 612. An annular space 627 may be disposed between an inside diameter of the sleeve 612 and an outside diameter of a core 616 disposed within the sleeve 612. The material may enter apertures 614 of a core 616, and exit the second interface 604. O-rings 618, 620 may seal the sleeve 612 to prevent the material from leaking from the annular space 627 out of the sleeve 612.

The integrated retaining ring 702 may couple the hub 608 and a core 616. The integrated retaining ring 702 may comprise one or more lock tabs (e.g., lock tab 710) coupled to the hub 608 that mate with along a notch 720 on the core 616. As shown, the notch 720 may be located adjacent or near the gripping surface 613. A more detailed discussion of portion 700 of the swivel elbow connector 600 is made with reference to FIG. 7 below.

Figure 7:
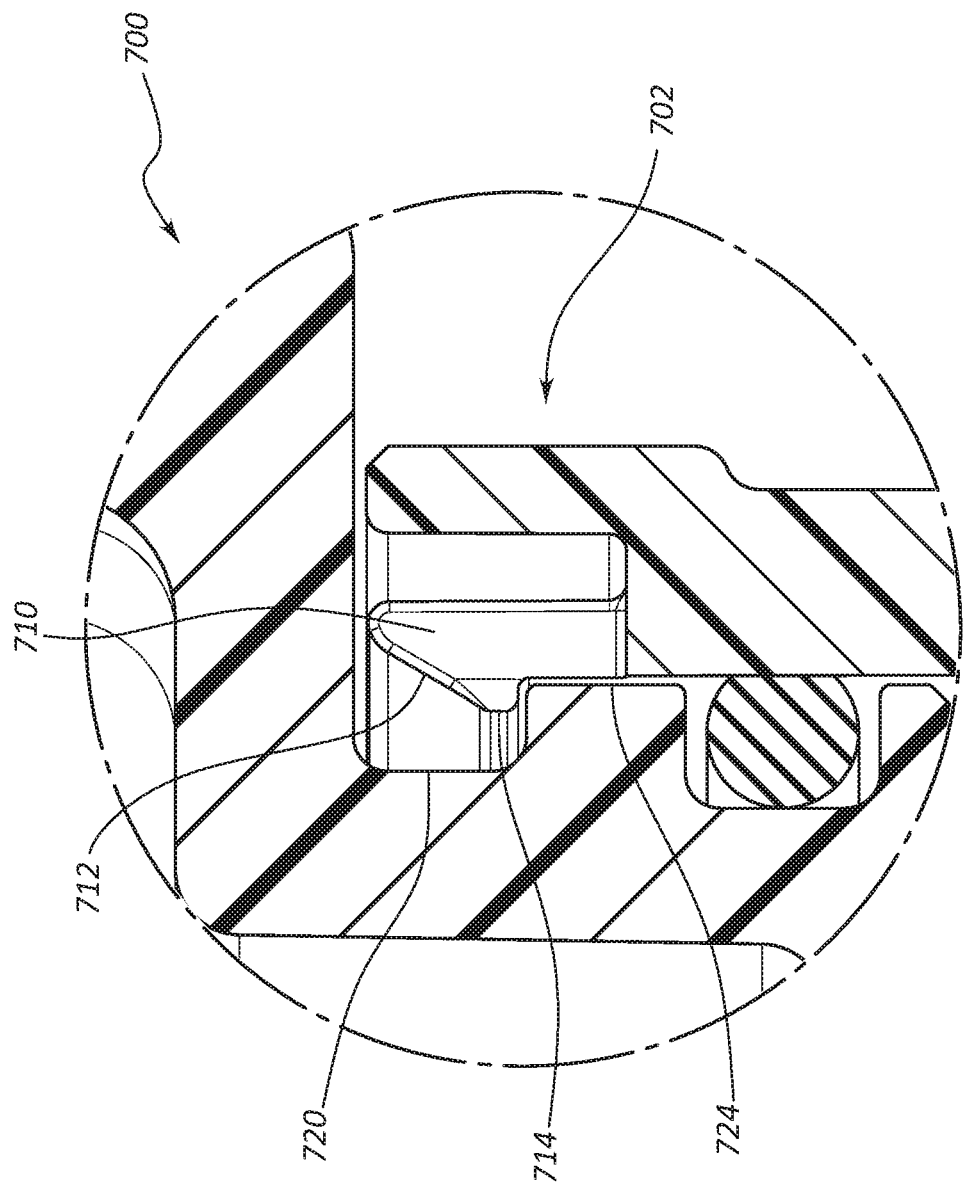
FIG. 7 is a close up view of a portion of the swivel elbow connector with an integrated retaining ring of FIG. 6.

FIG. 7 is a close up view of a portion 700 of the swivel elbow connector with an integrated retaining ring 702 of FIG. 6. As shown, the integrated retaining ring 702 may include a lock tab 710 that comprises a sloped interface 712 and a catch 714. The integrated retaining ring 702 may have a diameter slightly smaller than the core. The sloped interface 712 may receive the core, and allow an assembler to push the core through the retaining ring 702. The lock tab 710 may flex to accommodate the core. When the catch 714 reaches the slot 720 on the core, the lock tab may resume its original diameter. Thus, the catch 714 may settle into the notch 714 and be retained by the core's sidewall 724.

Figure 8:
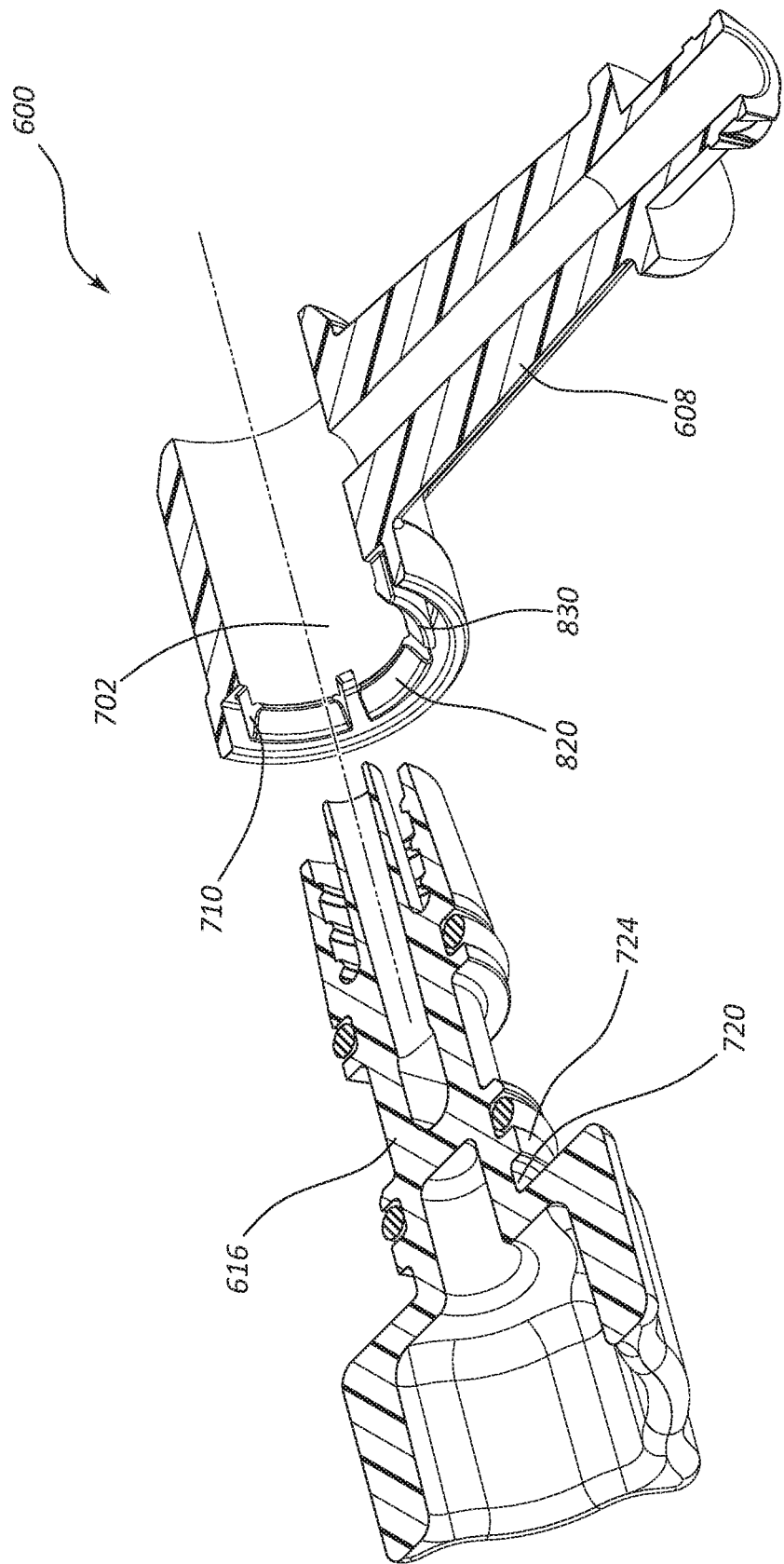
FIG. 8 is a partially exploded cross sectional view of the swivel elbow connector with an integrated retaining ring, of FIGS. 6 and 7.

FIG. 8 is a partially exploded cross sectional view of the swivel elbow connector 600 with an integrated retaining ring 702 of FIGS. 6 and 7. As shown, the integrated retaining ring 702 may be coupled to the hub 608. The retaining ring 702 may comprise a plurality of locking tabs (e.g., 710, 820, 830). The locking tabs 710, 820, and 830 may be disconnected from one another to allow each lock tab to flex.

The lock tabs 710, 820, and 830 may be configured to catch or latch in the notch 720 of the core 616. The notch 720 may be a groove along the entire circumference of the core 616. Alternatively, the notch 720 may be a series of groves that must be aligned with the lock tabs 710, 820, and 830.

An assembler may then slide the core 616 into the hub 608. The lock tabs 710, 820, and 830 may flex slightly to allow the core 616 to be pushed through. When the locking tabs 710, 820, and 830 reach the notch 720, the locking tabs 710, 820, and 830 may return to their original position, causing them to catch in the notch 720. Moreover, when the locking tabs 710, 820, and 830 catch they may retain the core. The lock tabs 710, 820, and 830 may limit the movement of the hub 608 with respect to the core 616, allowing the hub 608 to rotate with respect to the core 616 but not translate with respect to the core 616.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, it should be appreciated by one of skill in the art with the benefit of this disclosure that in the above description of embodiments, various features are sometimes grouped together in a single embodiment, figure, or description thereof for the purpose of streamlining the disclosure. This method of disclosure, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

We claim:

1. A medical connector, comprising:
a core having at least one aperture opening to a center cavity in the core;
a first interface mechanically coupled to the core and fluidly coupled with the center cavity in the core;
a hub comprising:
a hollow stem positioned at an angle relative to the first interface,
a second interface located at a proximal end of the hollow stem, and
a sleeve located at a distal end of the hollow stem surrounding the core and forming a fluid pathway for transferring a fluid through the second interface, the hollow stem, the hub, the at least one aperture in the core, and the first interface,
wherein the hub is selectively rotatable relative to the core and the first interface; and
a retaining ring to maintain the position of the sleeve relative to the core, the retaining ring comprising at least one sloped surface configured to slidably engage the core during assembly of the medical connector,
wherein the sleeve comprises a single cylindrical interior surface extending from a first end of the sleeve to a second end of the sleeve,
wherein the first interface comprises female threads,
wherein at least a portion of the retaining ring radially overlaps the female threads,
wherein the sloped surface of the retaining ring is disposed within an annular groove of the core, and
wherein the annular groove is disposed radially outward of the female threads.

2. The medical connector of claim 1, further comprising two O-rings to fluidly seal the sleeve to the core.

3. The medical connector of claim 1, further comprising a gripping surface mechanically coupled to the core and the first interface for rotating the core and the first interface.

4. The medical connector of claim 3, wherein the gripping surface comprises a plurality of grip tabs.

5. The medical connector of claim 1, wherein the sleeve is a hollow cylinder and the core is a cylindrical shape and disposed in the sleeve.

6. The medical connector of claim 5, wherein the sleeve and core are sized and positioned to create an annular space between a portion of the sleeve and the core.

7. The medical connector of claim 1, wherein the core has a plurality of apertures.

8. The medical connector of claim 1, wherein the first interface is a different type than the second interface.

9. The medical connector of claim 1, wherein the retaining ring is disposed between the sleeve and the first interface.

10. The medical connector of claim 1, wherein the retaining ring is integral with the sleeve.

11. The medical connector of claim 1, wherein the core comprises a tapered external surface extending proximally from a distal end of the core and
wherein the tapered external surface is disposed radially outward of the female threads.

12. The medical connector of claim 11, wherein the sloped surface of the retaining ring is configured to slidably engage the tapered external surface during assembly of the medical connector.

13. An adapter for a medical device, comprising:
a hub including a stem and a barrel, the barrel forming an open chamber, and the stem having a first interface and a first fluid pathway forming a port through a lateral surface of the barrel connecting the first interface to the chamber;
a core having at least one aperture opening to a second fluid pathway disposed within the chamber,
wherein the hub is selectively rotatable relative to the core;
at least two seals to fluidly seal both ends of the barrel to the core;
a second interface coupled to a distal end of the core, the second interface in fluid communication with the second fluid pathway;
a gripping surface mechanically coupled to a proximal end of the core to rotate the core; and
a fastener to secure the barrel between the fastener and the gripping surface, wherein the fastener comprises a plurality of longitudinally disposed deflectable members,
wherein the second interface comprises female threads,
wherein a maximum outside diameter of the second interface is less than a minimum inside diameter of the barrel, and
wherein the female threads are fixedly coupled to the core such that the female threads rotate with the core.

14. The medical adapter of claim 13, wherein the barrel and core are sized and positioned to create an annular space between a portion of the sleeve and the core.

15. The medical adapter of claim 13, wherein the fastener is a snap-fit retaining ring.

16. The medical adapter of claim 13, wherein the gripping surface comprises a plurality of grip tabs.

17. The medical adapter of claim 13, wherein the deflectable members deflect in a radial direction during assembly of the medical adapter.

18. The medical connector of claim 13, wherein at least a portion of the fastener radially overlaps the female threads.

19. The medical connector of claim 13, wherein the core comprises a tapered surface disposed radially outward of the female threads, and
   wherein the plurality of longitudinally deflectable members are configured to engage the tapered surface during assembly of the medical connector.

* * * * *